United States Patent [19]

Engel et al.

[11] 3,969,419
[45] July 13, 1976

[54] 3-(2-HALO-4-BIPHENYLYL)-1-BUTANOLS AND DERIVATIVES THEREOF

[75] Inventors: Wolfhard Engel; Helmut Teufel; Ernst Seeger; Günther Engelhardt, all of Biberach an der Riss, Germany

[73] Assignee: Boehringer Ingelheim GmbH, Ingelheim am Rhine, Germany

[22] Filed: Aug. 15, 1974

[21] Appl. No.: 497,716

[30] Foreign Application Priority Data
Aug. 16, 1973  Germany............... 2341506

[52] U.S. Cl. ............... 260/618 D; 260/295 R; 260/295.5 R; 260/389; 260/408; 260/469; 260/476 R; 260/488 CD; 260/515 A; 260/546; 260/611 A; 260/649 F; 260/149 DP; 424/266; 424/308; 424/311; 424/312; 424/345; 260/544 D
[51] Int. Cl.² ............... C07C 31/14; C07C 69/14; C07C 69/78; C07C 69/24
[58] Field of Search ..... 260/618 R, 476 R, 488 CD, 260/408, 618 D

[56] References Cited
UNITED STATES PATENTS

| | | | |
|---|---|---|---|
| 2,634,302 | 4/1953 | Seymour et al. | 260/618 R |
| 3,061,634 | 10/1962 | Palazzo | 260/618 R |
| 3,298,346 | 12/1975 | Seeger | 260/618 |
| 3,624,142 | 11/1971 | Shen et al. | 260/618 R |
| 3,801,654 | 4/1974 | Seeger et al. | 260/618 R |
| 3,859,256 | 1/1975 | Teufel et al. | 260/343.6 |

OTHER PUBLICATIONS

Burger, "Medicinal Chemistry", Wiley–Interscience, (1970), pp. 71, 72.

*Primary Examiner*—Jane S. Myers
*Attorney, Agent, or Firm*—Hammond & Littell

[57] ABSTRACT

Compounds of the formula formula

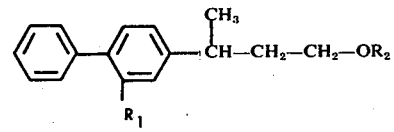

wherein $R_1$ is chlorine or fluorine, and
$R_2$ is hydrogen, alkanoyl of 1 to 10 carbon atoms, benzoyl, nicotinoyl or isonicotinoyl,
or, when $R_2$ contains a basic nitrogen atom, a non-toxic, pharmacologically acceptable salt thereof formed with an inorganic or organic acid; the compounds as well as the salts are useful as antiphlogistics.

3 Claims, No Drawings

3-(2-HALO-4-BIPHENYLYL)-1-BUTANOLS AND DERIVATIVES THEREOF

This invention relates to novel 3-(2-halo-4-biphenyl-yl)-1-butanols and derivatives thereof, as well as to methods of preparing these compounds.

More particularly, the present invention relates to a novel class of 3-(2-halo-4-biphenylyl)-1-butanols represented by the formula

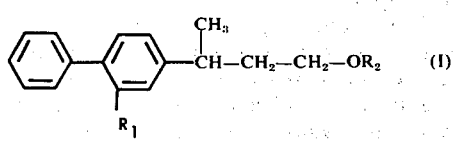

wherein $R_1$ is chlorine or fluorine, and $R_2$ is hydrogen, alkanoyl of 1 to 10 carbon atoms, benzoyl, nicotinoyl or isonicotinoyl, or, when $R_2$ contains a basic nitrogen atom, a non-toxic, pharmacologically acceptable salt thereof formed with an inorganic or organic acid.

The compounds embraced by formula I may be prepared by the following methods, among others:

METHOD A

By reduction of a compound of the formula

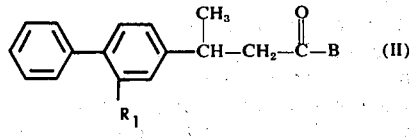

wherein $R_1$ has the meaning previously defined, and

B is hydroxyl, alkoxy, aralkoxy, aryloxy, acyloxy or halogen, with a complete hydride, whereby a compound of the formula I wherein $R_2$ is hydrogen is obtained.

Examples of preferred complex hydrides are lithium aluminum hydride, lithium borohydride or alkoxyaluminum hydrides, such as sodium-bis-(2-methoxyethoxy)-dihydroaluminate. However, sodium borohydride together with anhydrous aluminum chloride or with boron trifluoride may also be used.

A compound of the formula II, wherein B is halogen, may also be reduced with sodium borohydride by itself.

The reduction is performed in a suitable solvent, such as tetrahydrofuran, ether, dimethoxyethane, diethyleneglycol dimethylether, benzene or in mixtures thereof, at temperatures between 0° and 30°C.

METHOD B

By catalytic reduction of a compound of the formula

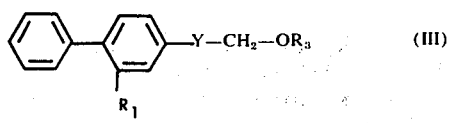

wherein $R_1$ has the meanings previously defined,

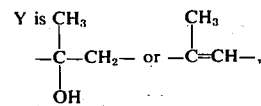

and $R_3$ has the meaning defined for $R_2$ and can additionally be α-arylalkyl-, α,α-diarylalkyl or triarylmethyl.

As catalysts, especially noble metal catalysts, such as palladium on coal or on barium sulfate or, if

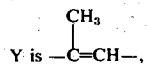

also Raney metals, such as Raney nickel or Raney cobalt, may be used.

The reduction is in general, performed in a solvent, for example in an alcohol, at temperatures between 0° and 100°C, preferably, however, at room temperature and at a hydrogen pressure of from 1 to 100 atmospheres, preferably from 3 to 10 atmospheres.

A compound of the formula III, wherein Y is

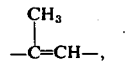

may also be reduced with nascent hydrogen, such as with hydrogen liberated by reaction of magnesium with methanol. The reduction is carried out at temperatures up to the boiling temperature of the solvent which is used, but preferably at room temperature.

When $R_3$ is α-arylalkyl, α,α-diarylalkyl or triarylmethyl, this group is subsequently removed by hydrogenation, for instance in the presence of palladium-on-coal in glacial acetic acid/methanol. The acetic acid ester which may be formed is hydrolized under alkaline conditions.

A compound of the formula I is obtained, wherein $R_2$ is hydrogen.

METHOD C

By reduction of a 3-(4-biphenylyl)-compound of the formula

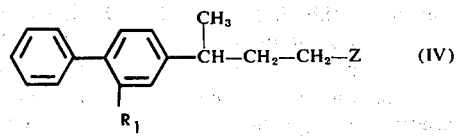

wherein $R_1$ has the meanings previously defined, and Z is hydroxyl which may optionally be esterified with an inorganic or organic acid, halogen, or —OMe, where Me is an alkali metal or an equimolar quantity of an alkaline earth metal atom, with a carboxylic acid derivative.

The esterification is, for example, performed by reaction of a compound of the formula IV with a carboxylic acid of the formula

 (V)

wherein $R_2$ has the meanings previously defined. The esterification is advantageously carried out in the presence of an organic solvent at elevated temperatures, preferably at temperatures above 60°C, optionally up to the boiling temperature of the solvent which is used. As solvents, preferably benzene, toluene, xylene, chloroform or other halogenated aliphatic hydrocarbons, such as ethylene chloride are used. It is of advantage, if the water released by the reaction is removed by means of azeotropic distillation; however, dehydrating agents, such as potassium pyrosulfate, may also be used. Favorable results can also be obtained by use of acid catalysts, such as toluenesulfonic acid, hydrochloric acid, sulfuric acid, phosphoric acid or thionyl chloride. Lower alkyl carboxylic acids of the formula V, such as formic acid or acetic acid, are preferably used in excess without further solvents.

An ester of the formula I, that is, where $R_2$ has the meanings previously defined except hydrogen, may also be prepared by reaction of an ammonium, alkali metal, alkaline earth metal, lead or silver salt of a carboxylic acid of the formula

 (VI)

wherein $R_3$ has the meanings defined for $R_2$ except hydrogen, and Me is an alkali metal, silver or a half equimolar quantity of an alkaline earth metal or lead atom, or Me$^{(+)}$ represents an ammonium ion, with a 1-halo-3-(4-biphenylyl)-butane of the formula

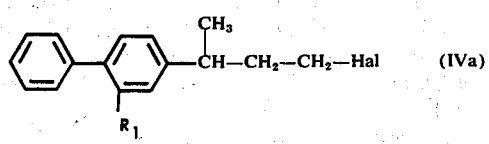 (IVa)

wherein $R_1$ has the meanings previously defined, and Hal is chlorine, bromine or iodine.

The reaction is performed in the presence of a solvent, such as benzene, toluene, xylene, ethylene chloride or another halogenated aliphatic hydrocarbon, in the presence of an ether, such as diethyl ether or dioxane, or in the presence of a dipolar aprotic solvent, such as dimethylformamide, dimethylsulfoxide, hexamethyl phosphoric acid triamide or acetone, at temperatures between 0° and 150°C, the mixture being heated, if necessary, in an agitator autoclave. The carboxylic acid salts are preferably used in a freshly precipitated state. A special embodiment is the reaction of the free carboxylic acid corresponding to the salt of the formula VI in the presence of silver oxide with the iodide of the formula IVa in xylene, preferably in an apparatus comprising a water trap, at elevated temperatures.

An ester of the formula I, that is, where $R_2$ has the meanings previously defined except hydrogen, may also be obtained by reaction of a carbinol of the formula IV with a carboxylic acid imidazolide of the formula

 (VII)

wherein $R_3$ has the meanings defined for $R_2$ except hydrogen.

The reaction is performed in the presence of an inert solvent at room temperature or at temperatures up to 150°C. As inert solvents, for example ethers, such as diethyl ether, dioxane or tetrahydrofuran, or cyclic aliphatic hydrocarbons may be used. If catalytical quantities of an alkali metal salt of the carbinol of the formula IV are present, a carboxylic acid ester of the formula I is formed with good yields already at room temperature.

An ester of the formula I may be also prepared by trans-esterification from a carboxylic acid ester of the formula

 (VIII)

wherein $R_2$ has the meanings previously defined, and $R_4$ is a lower alkyl, preferably methyl or ethyl, with a carbinol of the formula IV in the presence of a solvent. The trans-esterification is preferably carried out in the presence of a small quantity of an alkali metal, alkaline earth metal or aluminum alcoholate, preferably in the presence of a corresponding alcoholate of the carbinol of the formula IV, or of the formula $R_4OH$.

The trans-esterification is carried out at the boiling point of the reaction mixture. As solvents, especially toluene, xylene or ethylene chloride have proved to be suitable. The solvent is distilled off together with the alcohol of the formula $R_4OH$ which is formed by the reaction.

An ester of the formula I is also obtained by reaction of a carboxylic acid halide of the formula

 (IX)

wherein $R_3$ has the meanings defined for $R_2$ except hydrogen, and Hal is halogen, preferably chlorine or bromine, with an alcohol of the general formula IV, or with an alkali metal or alkaline earth metal salt of an alcohol of the formula

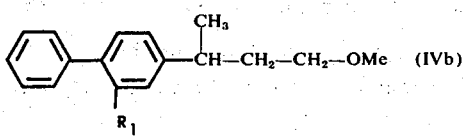 (IVb)

wherein $R_1$ has the meanings previously defined, and Me is an alkali metal atom or an equimolar quantity of an alkaline earth metal atom.

The reaction with an alcohol of the formula IV is preferably carried out in the presence of an organic solvent at temperatures between 20° and 150°C. As solvents, for example benzene, toluene, chlorinated aliphatic hydrocarbons, or aliphatic or cyclic ethers have proved to be suitable. The reaction proceeds at temperatures between 0° and 80°C if a tertiary organic base is present, and the tertiary organic base may at the same time serve as solvent. As tertiary organic bases, for example triethylamine or pyridine may be used.

The reaction with a salt of the formula IVb is preferably carried out in the presence of an organic solvent at temperatures between 0° and 150°C. As solvents, for example benzene, toluene, xylene or aliphatic straight or cyclic ethers have proved to be suitable.

An ester of the formula I is also formed by reaction of a carboxylic acid anhydride of the formula

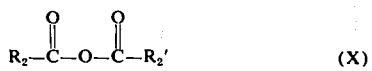   (X)

wherein $R_2$ has the meanings previously defined, and $R_2'$ has the meanings defined for $R_2$ except hydrogen, with a carbinol of the formula IV.

The reaction is performed at temperatures between 20° and 150°C, preferably in an organic solvent, such as benzene, toluene, xylene, ethylene chloride or pyridine. An excess of the carboxylic acid anhydride of the formula X may also be used as the solvent, especially when this carboxylic acid anhydride is low-molecular. Those compounds of the formula X, wherein $R_2$ is hydrogen and $R_2'$ lower alkyl or aralkyl, may also be used as starting materials. Such a mixed anhydride is reacted with a carbinol of the formula IV at temperatures between 0° and 60°C in the presence of a solvent, such as benzene, toluene or diethyl ether.

METHOD D

By reaction of a metal-organic compound of the formula

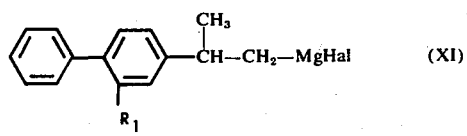   (XI)

wherein $R_1$ has the meanings previously defined, and Hal is chlorine, bromine or iodine, with formaldehyde or paraformaledhyde.

The reaction is carried out in the presence of a solvent suitable for Grignard reactions, for instance in the presence of an ether, such as diethyl ether or dioxane, at room temperature or at temperatures up to and including the boiling point of the solvent which is used. A compound of the formula I wherein $R_2$ is hydrogen is obtained by this method. Those compounds of the formula I wherein $R_2$ contains a basic nitrogen atom, are organic bases and form acid addition salts with inorganic or organic acids. Examples of non-toxic, pharmacologically acceptable acid addition salts are those formed with hydrochloric acid, hydrobromic acid, sulfuric acid, acetic acid, tartaric acid, fumaric acid, 8-chlorotheophylline or the like.

The starting compounds of the formula III wherein

Y is 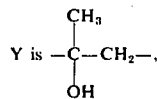, and $R_1$ and $R_3$ have the meanings defined above, may, for example, be obtained by reaction of a ketone of the formula

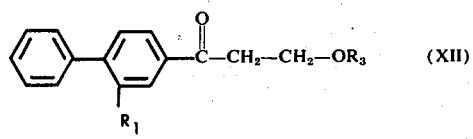   (XII)

wherein $R_1$ has the meanings previously defined, with a methyl magnesium halide. If $R_3$ in formula XII has the meanings defined for $R_2$ in formula I, a compound of the formula III wherein $R_3$ is hydrogen is obtained.

A compound of the formula III wherein Y is

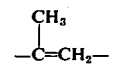

and $R_3$ is hydrogen, may be prepared by dehydration from a compound of the formula III wherein Y is

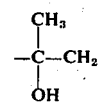

and $R_3$ is hydrogen. As dehydrating agents, especially hydrogen halide salts of tertiary organic bases may be used. As tertiary organic bases, for example pyridine, alkylpyridines, N,N-dialkylanilines or N-alkylpiperidines may be used. As hydrogen halides, especially hydrogen chloride and hydrogen bromide are suitable. Pyridine hydrochloride has proved to be particularly suitable as a dehydrating agent. The reaction may be carried out in the absence of a solvent. In some cases the presence of a solvent is of advantage. The compound of the formula III, wherein Y is

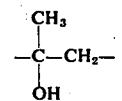

and $R_3$ is hydrogen, is heated with the dehydrating agent up to temperatures between 100° and 200°C. As solvents, for example toluene, xylene or o-dichlorobenzene may be used.

A starting compound of the formula II wherein B is other than halogen may, for example, be prepared by reduction of a compound of the formula III wherein Y is

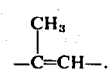.

The reduction may, for example, be effected catalytically, using a noble metal oxide, such as platinum oxide, as the catalyst. The reaction is advantageously carried out in the presence of a solvent, such as in methanol or ethanol, preferably at temperatures between 20° and 100°C and at slightly elevated pressure, such as at 2 to 10 atmospheres. From a compound of the formula II wherein Y is

and B is hydroxyl, a compound of the formula II wherein B is halogen or acyloxy, may subsequently be prepared, if desired, by methods described in the literature.

The starting compounds of the formula IV may be prepared by reduction of a compound of the formula II. The reduction is performed by means of a complex hydride, preferably with lithium aluminum hydride, lithium borohydride or an alkoxy aluminum hydride, such as sodium-bis-(2-methoxyethoxy)-dihydro-aluminate. However, sodium borohydride may also be used.

The starting compounds of the formulas IVb, V, VI, VII, VIII and IX are described in the literature or may be prepared by methods described in the literature. The symmetric carboxylic acid anhydrides of the formula X are also described in the literature or are accessible by methods described in the literature; the alkanoic acid-formic acid anhydrides of the formula X may be obtained by various methods, such as by the method of R. Schijf and W. Stevens, Rec. Trav. chim. Pays-Bas 85, 627 (1966).

The starting compounds of the formula IVa may, for example, be obtained by reaction of a carbinol of the formula IV with a phosphorus halide, such as phosphorus tribromide.

The halogen compounds from which the compounds of the formula XI are derived may be obtained analogous to methods described in the literature, for instance from the corresponding carbinols.

The following examples illustrate the present invention and will enable others skilled in the art to understand it more completely. It should be understood, however, that the invention is not limited solely to the particular examples given below.

Preparation of starting compound for method B:

EXAMPLE A

Ethyl 3-(2-fluoro-4-biphenylyl)-2-butenoate 42.8 gm (0.20 mol) of 4-acetyl-2-fluoro-biphenyl were added in small portions, while stirring, to a Reformatsky reagent prepared from 57.5 gm (0.88 mol) of zinc and 73.5 gm (0.44 mol) of bromoacetic acid ethyl ester in 500 ml of absolute ether/tetrahydrofuran (1:1), and the resulting mixture was refluxed for one hour. Then, 1 liter of water was added, the reaction mixture was acidified with dilute hydrochloric acid, and the organic layer was separated, extracted again with water and dried over sodium sulfate. The raw 3-(2-fluoro-4-biphenylyl)-3-hydroxy-butyric acid ethyl ester remaining after the solvent had been distilled off was refluxed in 330 ml of benzene with 45 gm (0.293 mol) of phosphorus trichloride for 10 minutes, whereupon the solvent was distilled off, water was added to the residue and the precipitated oil was taken up in ether. The ether solution was washed with water and an aqueous 5% sodium bicarbonate solution until neutral, dried, filtered through charcoal, and the solvent was distilled out of the filtrate. The residue, raw 3-(2-fluoro-4-biphenylyl)-2-butenoic acid ethyl ester (39.9 gm, 70% of theory), was used as a starting compound without further purification.

Preparation of end products of the formula I:

EXAMPLE 1

3-(2-Fluoro-4-biphenylyl)-1-butanol by method A

A solution of 25.83 gm (0.10 mol) of 3-(2-fluoro-4-biphenylyl)-butyric acid in 100 ml of absolute tetrahydrofuran was added dropwise at room temperature to a stirred suspension of 2.85 gm (0.075 mol) of lithium aluminum hydride in 100 ml of absolute tetrahydrofuran, the resulting mixture was stirred for 60 minutes more at room temperature and for 30 minutes at 30°–35°C, and then ethyl acetate was added dropwise until no more exothermic reaction occurred. The reaction mixture was then stirred for 15 minutes at room temperature, and thereafter first 50 ml of water and then aqueous 5% hydrochloric acid were added dropwise, accompanied by exterior cooling with ice water, until the precipitate first formed dissolved. The solution was stirred into 2 liters of water, extracted exhaustively with ether, and the combined ether extracts were washed successively with water, saturated aqueous sodium bicarbonate solution and again with water, dried over sodium sulfate, filtered, and evaporated. 18.0 gm (74% of theory) of colorless 3-(2-fluoro-4-biphenylyl)-1-butanol of the formula

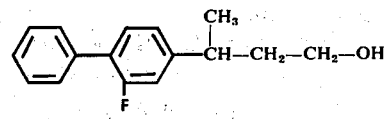

which had a melting point of 72°C after recrystallization from cyclohexane.

EXAMPLE 2

Using a procedure analogous to that described in Example 1, 31% of theory of colorless crystalline 3-(2-chloro4-biphenylyl)-1-butanol, m.p. 66°–67°C after recrystallization from cyclohexane/petroleum ether (volumetric ratio 1:1) was obtained from 3-(2-chloro-4-biphenylyl)-butyric acid.

EXAMPLE 3

3-(2-Fluoro-4-biphenylyl)-1-butyl pelargonate by method C

A mixture consisting of 6.11 gm (0.025 mol) of 3-(2-fluoro-4-biphenylyl)-1-butanol, 4.27 gm (0.027 mol) of pelargonic acid, 0.25 gm of p-toluene-sulfonic acid and 50 ml of absolute toluene was refluxed in a vessel equipped with a water trap until no more water separated out. Thereafter, the reaction solution was diluted with ether, the organic solution was extracted with water, dilute ammonia and again with water, dried over sodium sulfate, and the solvent was distilled off. 6.45 gm (67% of theory) of the ester of the formula

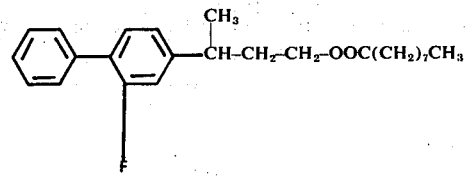

having a boiling point of 183°–190°C at 0.1 mm Hg were obtained.

EXAMPLE 4

3-(2-Fluoro-4-biphenylyl)-1-butyl caprylate by method C 6.15 gm (66% of theory) of 3-(2-fluoro-4-biphenylyl)-1-butyl caprylate, b.p. 178°–185°C at 0.15 mm Hg, were obtained by heating 3.89 gm (0.027 mol) of caprylic acid with 6.11 gm (0.025 mol) of 3-(2-fluoro-4-biphenyly)-1-butanol under the conditions described in Example 3.

EXAMPLE 5

3-(2-Fluoro-4-biphenylyl)-1-butyl isonicotinate 10.27 gm (0.045 mol) of isonicotinic acid anhydride were added to a stirred solution of 10.00 gm (0.041 mol) of 3-(2-fluoro-4-biphenylyl)-1-butanol in 50 ml of absolute pyridine, the resulting mixture was heated at 50°C for 2 hours, 200 ml of water were added and the mixture was exhaustively extracted with ether. The combined ether extracts were washed with water, with a saturated aqueous sodium bicarbonate solution and again with water, dried and evaporated. The residue was distilled in vacuo, yielding 9.02 gm (63% of theory) of the ester of the formula

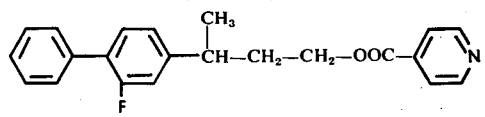

which had a boiling point of 186°–190°C at 0.1 mm Hg.

The ester was dissolved in ether, and the solution was acidified with ethereal hydrochloric acid, yielding the hydrochloride of the ester, m.p. 120°C after recrystallization from ethyl acetate/acetone (9:1).

EXAMPLE 6

3-(2-Fluoro-4-biphenylyl)-1-butyl benzoate by method C

Using a procedure analogous to that described in Example 3, 5.85 gm (67% of theory) of the ester of the formula

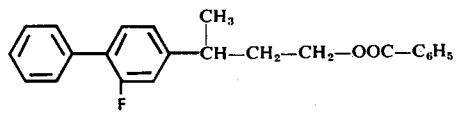

having a boiling point of 181°–185°C at 0.05 mm Hg were obtained by refluxing a mixture consisting of 6.11 gm (0.025 mol) of 3-(2-fluoro-4-biphenylyl)-1-butanol, 6.20 gm (0.051 mol) of benzoic acid, 0.5 gm of p-toluene-sulfonic acid and 40 ml of toluene until no more water separated out.

EXAMPLE 7

3-(2-Chloro-4-biphenylyl)-1-butyl formate by method C

A solution of 10.0 gm (0.038 mol) of 3-(2-chloro-4-biphenylyl)-1-butanol in 50 ml (about 1.3 mols) of formic acid was refluxed for eight hours. Thereafter, the reaction mixture was evaporated, the residue was repeatedly admixed with toluene which was then distilled off, the residue was taken up in ether, and the solution was washed with water until neutral and then evaporated. The residual oily product was distilled in vacuo, yielding 9.4 gm (86% of theory) of the desired ester in the form of a thin oil having a boiling point of 138°–144°C at 0.07 mm Hg.

EXAMPLE 8

3-(2-Chloro-4-biphenylyl)-1-butyl acetate by method C

A solution of 3.92 gm (0.05 mol) of acetyl chloride in 20 ml of absolute toluene was allowed to flow into a solution of 10.0 gm (0.038 mol) of 3-(2-chloro-4-biphenylyl)-1-butanol and 5.0 gm (0.05 mol) of triethylamine in 100 ml of absolute toluene at room temperature; the resulting mixed solution was then stirred for several hours and was subsequently heated for 1 hour at 100°C. Thereafter, the reaction mixture was allowed to cool, water was then added, the toluene phase was separated, and the aqueous phase was extracted with ether. The combined organic solutions were washed until neutral, dried and evaporated, and the residue was distilled in vacuo, yielding 9.21 gm (80% of theory) of the desired ester in the form of a colorless oil having a boiling point of 145°–152°C at 0.06 mm Hg.

EXAMPLE 9

Using a procedure analogous to that described in Example 3, 10.8 gm (91% of theory) of 3-(2-fluoro-4-biphenylyl)-1-butyl caproate, a colorless oil having a boiling point of 160°–165°C at 0.1 mm Hg, were obtained by refluxing a mixture consisting of 4.30 gm (0.037 mol) of caproic acid, 8.50 gm (0.0348 mol) of 3-(2-fluoro-4-biphenylyl)-1-butanol, 0.35 gm of p-toluene-sulfonic acid and 70 ml of anhydrous toluene.

EXAMPLE 10

Using a procedure analogous to that described in Example 8, 53% of theory of 3-(2-fluoro-4-biphenylyl)-1-butyl acetate, b.p. 143°–148°C at 0.1 mm Hg, was obtained from 3-(2-fluoro-4-biphenylyl)-1-butanol and acetyl chloride in the presence of triethylamine.

The compounds of the present invention, that is, those embraced by formula I and, when $R_2$ contains a basic nitrogen atom, their non-toxic, pharmacologically acceptable acid addition salts, have useful pharmacodynamic properties. More particularly, the compounds of the instant invention exhibit very effective antiphlogistic activities in warm-blooded animals, such as rats.

The compounds of the present invention were tested for antiphlogistic activity, ulcerogenic activity and acute toxicity in the manner described below, and representative results of these tests are shown in the tables, where A = 3-(2-fluoro-4-biphenylyl)-1-butanol, B = 3-(2-fluoro-4-biphenylyl)-1-butyl isonicotinate hydrochloride, and C = 3-(2-chloro-4-biphenylyl)-1-butanol.

The compounds were tested for their anti-exudative effects on the kaolin edema and carrageenin edema of the hind paws of the rat, for their ulcerogenicity and for their acute toxicity by oral administration to rats.

The kaolin edema was induced according to the method of Hillebrecht [Arzneimittel-Forsch. 4, 607 (1954)] by subplantary injection of 0.05 ml of a 10% suspension of kaolin in a 0.85% sodium chloride solution. The measurement of the thickness of the paws was done by using the technique of Doepfner and Cerletti (Int. Arch. Allergy, Immunol. 12, 89 (1958)).

Male FW 49-rats of an average weight of 120–150 gm were orally treated with the test compounds 30 minutes before inducement of the edema with the aid of a esophageal tube. Five hours after the provocation of the edema the averaged values of the swelling caused in the paws of the rats treated with the test compounds were compared with those values measured on blind-treated control animals. By graphic extrapolation the dose leading to a 35% reduction of the swelling ($ED_{35}$) was calculated from the percent reduction values measured by administration of different doses.

The provocation of the carrageenin edema was effected according to the method of Winter et al. [Proc. Soc. exp. Biol. Med. 111, 544 (1962)] by subplantary injection of 0.05 ml of a 1% solution of carrageenin in a 0.85% solution of sodium chloride. The test compounds were orally administered 60 minutes before the provocation of the edema.

For the calculation of the reductive effect on the edema, the values measured three hours after the provocation of the edema were used. All the other details were the same as described above in the case of the kaolin edema.

The tests for ulcerogenic activity were effected on FW 49-rats of both sexes (ratio 1:1) having a body weight of 130 to 150 gm. The animals were given the substances on three subsequent days, once each day, as a trituration in tylose by way of an esophageal tube.

The animals were killed four hours after the last administration; the stomach and duodenal mucosa were investigated for ulcers.

From the percentage of animals showing at least one ulcer after administration of different doses, the $ED_{50}$-value was calculated according to the method of Litchfield and Wilcoxon [J. Pharmacol. exp. Therap. 96, 99 (1949)].

After oral administration to male and female FW 49-rats (ratio 1:1) having an average body weight of 135 gm, the acute toxicity ($LD_{50}$) was determined. The substances were administered orally as a trituration in tylose.

The calculation of the $LD_{50}$-values was effected, as far as possible, according to the method of Litchfield and Wilcoxon, based on the percentage of animals which died within 14 days after administration of the different doses.

The therapeutic indices, as a measure for the therapeutic usefulness, were calculated by forming the quotient of the $ED_{50}$-value for the ulcerogenicity or of th $LD_{50}$-value and the $ED_{35}$-value derived from the tests for anti-exudative activity against the kaolin and carrageenin edema.

TABLE I

| Compound | kaolin edema $ED_{35}$ per os mgm/kg | carrageenin edema $ED_{35}$ per os mgm/kg | Average anti-exudative $ED_{35}$ per os mgm/kg | acute toxicity in the rat $LD_{50}$ per os mgm/kg | confidence limits (95% probability) | Therapeutic ratio $LD_{50}$/aver.$ED_{35}$ |
|---|---|---|---|---|---|---|
| A | 17.0 | 8.5 | 12.75 | 825 | 625 – 1689 | 64.7 |
| B | 20.0 | 13.0 | 16.5 | 1530 | 1040 – 2250 | 92.7 |
| C | — | 17 | 17 * | >1600 | – ** | >94.1 |

* only from carrageenin edema
** at 1600 mgm/kg 1 out of 10 animals died.

TABLE II

| Compound | Average antiexudative $ED_{35}$ mgm/kg | ulcerogenic activity in the rat $ED_{50}$ per os mgm/kg | confidence limits (95% probability) | Therapeutic index Ratio of ulcerogenic activity to antiexudative activity $ED_{50}/ED_{35}$ |
|---|---|---|---|---|
| A | 12.75 | 30.5 | 16.94 – 54.90 | 2.39 |
| B | 16.5 | 61 | 40.66 – 91.50 | 3.70 |
| C | 17 * | 36.6 | 23.61 – 56.73 | 2.15 |

* only from carrageenin edema

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antiphlogistic dosage unit of the compounds according to the present invention is from 0.83 to 6.67 mgm/kg body weight, preferably 1.33 to 5.0 mgm/kg body weight. The daily dose rate is from 1.66 to 16.7 mgm/kg body weight, preferably 2.5 to 10 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 11

Tablets

The tablet composition is compounded from the following ingredients:

| | |
|---|---|
| 3-(2-Fluoro-4-biphenylyl)-1-butanol | 50.0 parts |
| Corn starch | 247.0 parts |
| Polyvinylpyrrolidone | 10.0 parts |
| Magnesium stearate | 3.0 parts |
| Total | 310.0 parts |

Preparation

The butanol compound and the corn starch are intimately admixed with each other, the mixture is granulated with an aqueous 14% solution of the polyvinylpyrrolidone through 1.5 mm-mesh screen, the granulate is dried at 45°C and again passed through the screen, and dry granulate is admixed with the magnesium stearate, and the composition is compressed into 310 mgm-tablets in a conventional tablet-making machine. Each tablet contains 50 mgm of the butanol compound and is an oral dosage unit composition with effective antiphlogistic action.

EXAMPLE 12

Coated pills

The pill core composition is compounded from the following ingredients:

| | |
|---|---|
| 3-(2-Fluoro-4-biphenylyl)-1-butanol | 100.0 parts |
| Corn starch | 170.0 parts |
| Gelatin | 8.0 parts |
| Talcum | 18.0 parts |
| Magnesium stearate | 4.0 parts |
| Total | 300.0 parts |

Preparation

The butanol compound and the corn starch are intimately admixed with each other, the mixture is granulated with an aqueous 10% solution of the gelatin through a 1.5 mm-mesh screen, the granulate is dried at 45°C and again passed through the screen, the dry granulate is admixed with the talcum and the magnesium stearate, and the composition is compressed into 300 mgm-pill cores which are subsequently coated with a thin shell consisting essentially of a mixture of sugar and talcum and finally polished with beeswax. Each coated pill contains 100 mgm of the butanol compound and is an oral dosage unit composition with effective antiphlogistic action.

EXAMPLE 13

Gelatin capsules

The capsule filler composition is compounded from the following ingredients:

| | |
|---|---|
| 3-(2-Fluoro-4-biphenylyl)-1-butanol | 200.0 parts |
| Corn starch | 190.0 parts |
| Colloidal silicic acid | 6.0 parts |
| Magnesium stearate | 4.0 parts |
| Total | 400.0 parts |

Preparation

The ingredients are intimately admixed with each other, and 400 mgm-portions of the mixture are filled into No. 1 gelatin capsules. Each capsule contains 200 mgm of the butanol compound and is an oral dosage unit composition with effective antiphlogistic action.

EXAMPLE 14

Suppositories

The suppository composition is compounded from the following ingredients:

| | |
|---|---|
| 3-(2-Chloro-4-biphenylyl)-1-butanol | 200.0 parts |
| Suppository base (e.g. cocoa butter) | 1450.0 parts |
| Total | 1650.0 parts |

Preparation

The finely pulverized butanol compound is blended with the aid of an immersion homogenizer into the suppository base which had previously been melted and cooled to 40°C. 1650 mgm-portions of the composition are poured into cooled suppository molds and allowed to harden therein. Each suppository contains 200 mgm of the butanol compond and is a rectal dosage unit composition with effective antiphlogistic action.

EXAMPLE 15

Suspension

The suspension is compounded from the following ingredients:

| | |
|---|---|
| 3-(2-Chloro-4-biphenylyl)-1-butyl isonicotinate hydrochloride | 4.0 parts |
| Dioctyl sodium sulfosuccinate (DONSS) | 0.02 parts |
| Benzoic acid | 0.1 parts |
| Sodium cyclamate | 0.2 parts |
| Colloidal silicic acid | 1.0 parts |
| Polyvinylpyrrolidone | 0.1 parts |
| Glycerin | 25.0 parts |
| Flavoring | 0.1 parts |
| Distilled water q.s.ad | 100.0 parts by vol. |

Preparation

The DONSS, the benzoic acid, the sodium cyclamate and the polyvinylpyrrolidone are successively dissolved in a sufficient amount of distilled water at 70°C, and the glycerin and colloidal silicic acid are added to the solution. The mixture is cooled to room temperature, the finely pulverized isonicotinate salt is suspended therein by means of an immersion homogenizer, the flavoring is added, and the composition is diluted with additional distilled water to the indicated volume. 5 ml of the resulting aqueous suspension contain 200 mgm of the isonicotinate salt and are an oral dosage unit composition with effective antiphlogistic action.

Analogous results are obtained when any one of the other compounds embraced by formula I or, when $R_2$ contains a basic nitrogen atom, a non-toxic acid addition salt thereof is substituted for the particular butanol compound in Examples 11 through 15. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.
We claim:
1. A compound of the formula
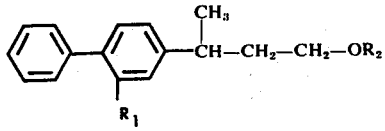
wherein $R_1$ is chlorine or fluorine, and
$R_2$ is hydrogen, alkanoyl of 1 to 10 carbon atoms or benzoyl.
2. The compound of claim 1 which is 3-(2-fluoro-4-biphenylyl)-1-butanol.
3. The compound of claim 1 which is 3-(2-chloro-4-biphenylyl)-1-butanol.
* * * * *